(12) United States Patent
Bilitz

(10) Patent No.: US 12,733,947 B2
(45) Date of Patent: Sep. 15, 2026

(54) ULTRASONIC THERAPY CATHETER SYSTEMS AND WIRE CONNECTOR ASSEMBLIES

(71) Applicant: KONINKLIJKE PHILIPS N.V., Eindhoven (NL)

(72) Inventor: Mark Bilitz, Plymouth, MN (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1001 days.

(21) Appl. No.: 17/911,687

(22) PCT Filed: Mar. 16, 2021

(86) PCT No.: PCT/EP2021/056581
§ 371 (c)(1),
(2) Date: Sep. 15, 2022

(87) PCT Pub. No.: WO2021/185788
PCT Pub. Date: Sep. 23, 2021

(65) Prior Publication Data

US 2023/0138253 A1 May 4, 2023

Related U.S. Application Data

(60) Provisional application No. 62/990,502, filed on Mar. 17, 2020.

(51) Int. Cl.
*A61B 17/22* (2006.01)
*A61B 17/00* (2006.01)

(52) U.S. Cl.
CPC .................. *A61B 17/22012* (2013.01); *A61B 2017/00477* (2013.01); *A61B 2017/00526* (2013.01); *A61B 2017/22015* (2013.01)

(58) Field of Classification Search
CPC ........ A61B 17/22012; A61B 17/00526; A61B 2017/22015; A61B 2017/22014; A61B 2017/00477; B06B 3/00
See application file for complete search history.

(56) References Cited

U.S. PATENT DOCUMENTS 5,507,738 A 4/1996 Ciervo
2002/0055754 A1 5/2002 Ranucci
2004/0158151 A1 8/2004 Ranucci
(Continued)

FOREIGN PATENT DOCUMENTS

CN 107510491 A 12/2017

OTHER PUBLICATIONS

International Search Report and Written Opinion Dated Jun. 29, 2021 For International Application No. PCT/EP2021/056581 Filed Mar. 16, 2021.

*Primary Examiner* — J. San Martin

(57) ABSTRACT

A wire connector assembly for an ultrasonic therapy catheter system including an ultrasound generator is presented. The wire connector assembly includes a sonic connector that is configured to couple to the ultrasound generator and receive ultrasonic energy therefrom. The sonic connector includes a body having a passageway that extends therethrough, and the passageway includes a tapered surface. The wire connector assembly further includes a wire that engages the tapered surface and extends outwardly from the passageway. The wire is configured to receive ultrasonic energy from the sonic connector.

15 Claims, 9 Drawing Sheets

(56) References Cited

U.S. PATENT DOCUMENTS

| | | | | |
|---|---|---|---|---|
| 2006/0095015 | A1 | 5/2006 | Hobbs | |
| 2006/0161098 | A1 | 7/2006 | Nita | |
| 2006/0253050 | A1 * | 11/2006 | Yoshimine | A61H 23/0245 601/2 |
| 2007/0066978 | A1 | 3/2007 | Schafer | |
| 2013/0253387 | A1 | 9/2013 | Bonutti | |
| 2014/0358134 | A1 | 12/2014 | Appling | |

* cited by examiner 400
426
428
412
432
422
420
404
434
410
406
430
418
416
414
408
424
402
7
7
406
412

ULTRASONIC THERAPY CATHETER SYSTEMS AND WIRE CONNECTOR ASSEMBLIES

CROSS-REFERENCE TO RELATED APPLICATION

This application is the U.S. National Phase application under 35 U.S.C. § 371 of International Application No. PCT/EP2021/056581 filed Mar. 16, 2021, which claims the benefit of U.S. Provisional Patent Application No. 62/990,502 filed Mar. 17, 2020. These applications are hereby incorporated by reference herein.

FIELD OF THE DISCLOSURE

The devices and methods described herein generally relate to vascular catheter systems, such as catheter systems that deliver therapeutic energy to occlusive materials, such as thrombus.

BACKGROUND

Thrombosis is a medical condition that results from the formation of a blood clot, or thrombus, within a vessel. Thrombi often develop in the valves, legs, or other lower abdomen (that is, deep vein thrombosis), but may occur in other vessels. The clot is typically formed from a pooling of blood within the vein due to abnormally long periods of rest, for example, when an individual is bed ridden following surgery or suffering a debilitating illness. In addition, thrombi also often develop near atherosclerotic plaque.

Embolisms occur when obstructive materials, such as a thrombus, travels around the body and lodges itself in an organ. For example, a pulmonary embolism is a blockage of the blood supply to the lungs that may cause hypoxia and cardiac failure. The formation of thrombi can lead to an embolism that may lead to serious health issues, including death. As another example, strokes occur when an embolus blocks an artery supplying blood to the brain, thus depriving the brain tissue of oxygen. Without oxygen, brain cells begin to die.

A variety of interventional methods and catheter devices are available to treat thrombi. For example, some catheter systems deliver ultrasonic energy to pulverize obstructions and permit subsequent aspiration of pulverized materials. An example of a portion of such a catheter system is shown in FIG. 1. More specifically, FIG. 1 illustrates a wire connector assembly 100 that couples to an ultrasound generator (not shown), commonly referred to as an ultrasonic "horn", via a threaded surface 102. The threaded surface 102 is a portion of a sonic connector 104 that couples the ultrasound generator to an elongated wire 106 that enters the vasculature of a subject, typically inside the lumen of a sheath (not shown). The wire 106 receives and transmits ultrasonic energy to pulverize obstructions within the subject.

However, ultrasonic therapy catheter systems, including those having the wire connector assembly 100 illustrated in FIG. 1, typically have one or more drawbacks. More specifically, the sonic connector 104 is typically provided as a relatively long component (more specifically, about 1.2 inches long) to facilitate resonance upon receiving ultrasonic energy. This length introduces several manufacturing challenges. For example, using a machining process to form the sonic connector 104, which typically comprises titanium grade 5, is relatively difficult and expensive. As another example, a simple manufacturing process for coupling the wire 106 to the sonic connector 104 includes forming a shallow blind hole 108 in the distal end 110 and crimping the wire 106 to the sonic connector 104 in the blind hole 108. Such a connection is typically secure, but not necessarily uniform. As such, the crimped connection may create a stress concentration, which may lead to wire failure. As another example, the length of the sonic connector 104 may cause misalignment between the wire 106 and the threaded surface 102. More specifically, the centers of the wire 106 and the threaded surface 102 may be misaligned due to tolerances and/or machining variations. This misalignment may cause transverse motion of the wire 106 and possible wire failure. As another example, the wire 106 is crimped to the sonic connector 104 proximally from the node of the ultrasonic horn, which is disposed at its distal end. This may cause relatively inefficient transmission of ultrasonic energy from the horn to the wire 106. As another drawback, the sonic connector 104 includes several abrupt size transitions, which can create stress concentrations.

Accordingly, improved ultrasonic therapy catheter systems and wire connector assemblies are needed.

SUMMARY

The present disclosure presents a wire connector assembly for an ultrasonic therapy catheter system including an ultrasound generator. The wire connector assembly includes a sonic connector that is configured to couple to the ultrasound generator and receive ultrasonic energy therefrom. The sonic connector includes a body having a passageway that extends therethrough, and the passageway includes a tapered surface. The wire connector assembly further includes a wire that engages the tapered surface and extends outwardly from the passageway. The wire is configured to receive ultrasonic energy from the sonic connector.

The wire connector assembly according to the previous paragraph, wherein the wire includes a proximal end portion including an engagement feature, and the engagement feature engages the tapered surface of the passageway of the sonic connector.

The wire connector assembly according to any of the previous paragraphs, wherein the sonic connector further includes a longitudinal axis aligned with the passageway, and an ultrasound generator engagement surface that is configured to engage the ultrasound generator. The ultrasound generator engagement surface is aligned with the engagement feature relative to the longitudinal axis.

The wire connector assembly according to any of the previous paragraphs, wherein the engagement feature includes a ball.

The wire connector assembly according to any of the previous paragraphs, wherein the wire further includes an elongated portion coupled to the engagement feature, wherein the passageway includes a proximal passageway portion including the tapered surface and a distal passageway portion coupled to the proximal passageway portion, and the distal passageway portion slip fittingly receives the elongated portion of the wire.

The wire connector assembly according to any of the previous paragraphs, wherein the sonic connector includes a longitudinal axis aligned with the passageway, and the sonic connector has a length along the longitudinal axis of substantially 0.7 inches.

The present disclosure also presents a method of manufacturing a wire connector assembly for an ultrasonic therapy catheter system. The method includes providing a sonic connector, the sonic connector includes a body having a passageway extending therethrough, and the passageway includes a tapered surface. The method further includes providing a wire and coupling the wire to the sonic connector such that the wire engages the tapered surface and extends outwardly from the passageway.

The method according to the previous paragraph, wherein providing the wire includes providing an elongated portion; providing an engagement feature; and coupling the engagement feature to the elongated portion; and wherein and coupling the wire to the sonic connector includes engaging the engagement feature with the tapered surface.

The method according to any of the previous paragraphs, wherein coupling the engagement feature to the elongated portion includes at least one of welding, crimping, and bonding the engagement feature to the elongated portion.

The method according to any of the previous paragraphs, wherein coupling the engagement feature to the elongated portion includes melting a proximal end portion of the wire.

The method according to any of the previous paragraphs, wherein coupling the wire to the sonic connector includes moving the sonic connector relative to the wire such that the wire passes through a proximal opening of the passageway, extends outwardly from a distal opening of the passageway, and the engagement feature engages the tapered surface.

The method according to any of the previous paragraphs, wherein the sonic connector includes a longitudinal axis aligned with the passageway and an ultrasound generator engagement surface configured to engage an ultrasound generator of the ultrasonic therapy catheter system, and wherein engaging the engagement feature with the tapered surface includes aligning the engagement feature with the ultrasound generator engagement surface relative to the longitudinal axis.

The method according to any of the previous paragraphs, wherein coupling the wire to the sonic connector further includes positioning a joining material in a proximal portion of the passageway including the tapered surface.

The method according to any of the previous paragraphs, wherein the engagement feature includes a ball.

The method according to any of the previous paragraphs, wherein the sonic connector includes a longitudinal axis aligned with the passageway and a length along the longitudinal axis of substantially 0.7 inches.

The phrases “at least one”, “one or more”, and “and/or” are open-ended expressions that are both conjunctive and disjunctive in operation. For example, each of the expressions “at least one of A, B and C”, “at least one of A, B, or C”, “one or more of A, B, and C”, “one or more of A, B, or C” and “A, B, and/or C” means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

The term “a” or “an” entity refers to one or more of that entity. As such, the terms “a” (or “an”), “one or more” and “at least one” may be used interchangeably herein. It is also to be noted that the terms “comprising”, “including”, and “having” may be used interchangeably.

The term “means” as used herein shall be given its broadest possible interpretation in accordance with 35 U.S.C. Section 112(f). Accordingly, a claim incorporating the term “means” shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout this disclosure is deemed to include each and every lower numerical limitation as an alternative, as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure may be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

Before any embodiments of the disclosure are explained in detail, it is to be understood that the disclosure is not limited in its application to the details of construction and the arrangement of components set forth in the following description or illustrated in the following drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The present disclosure relates generally to vascular catheter systems, devices, and methods for delivering therapeutic energy to occlusive materials, such as thrombus. The present disclosure also generally relates to methods of manufacturing such systems and devices.

Figure 1:
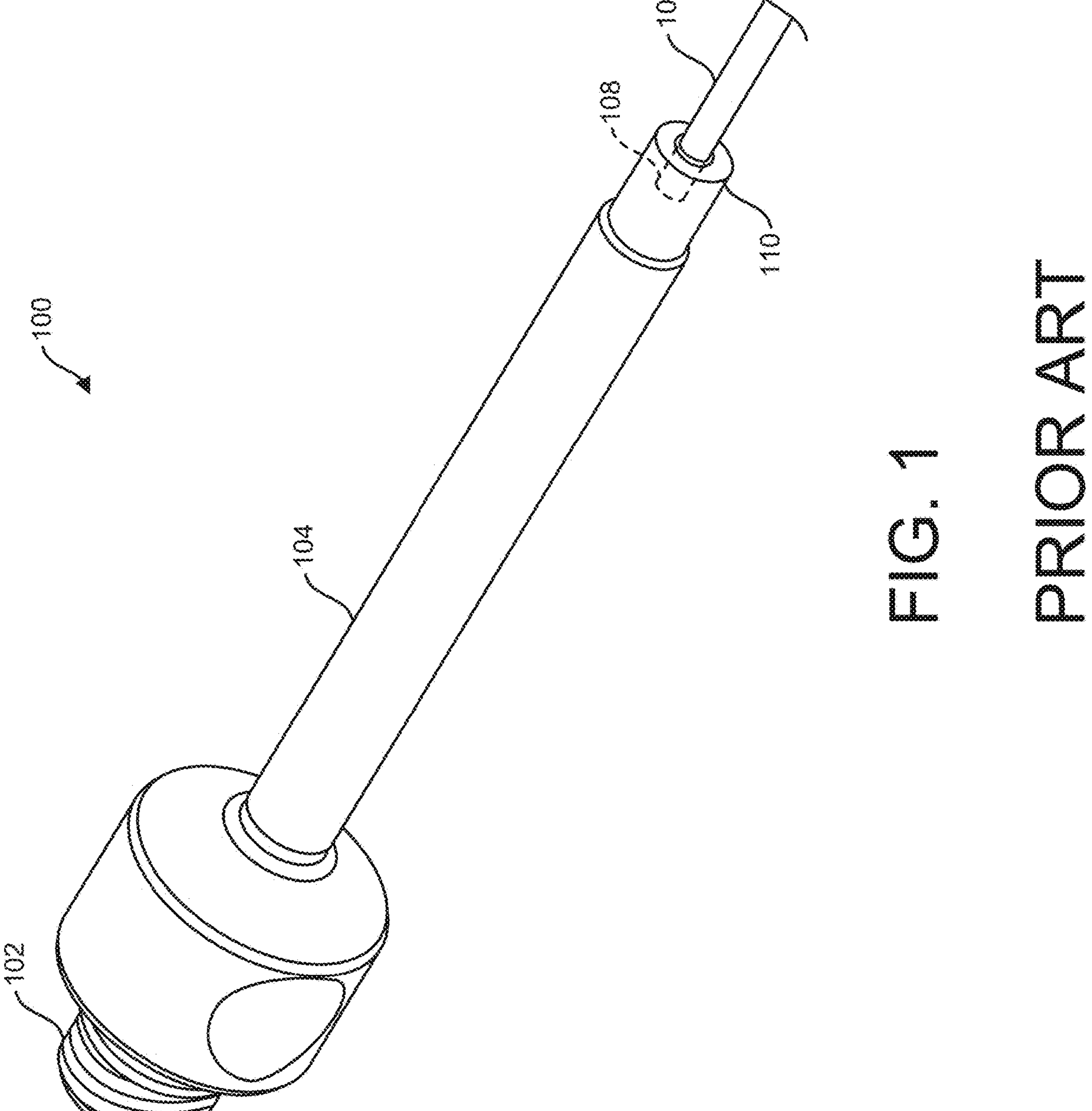
FIG. 1 is a perspective view of a wire connector assembly of an ultrasonic therapy catheter system according to the prior art.
Figure 2:
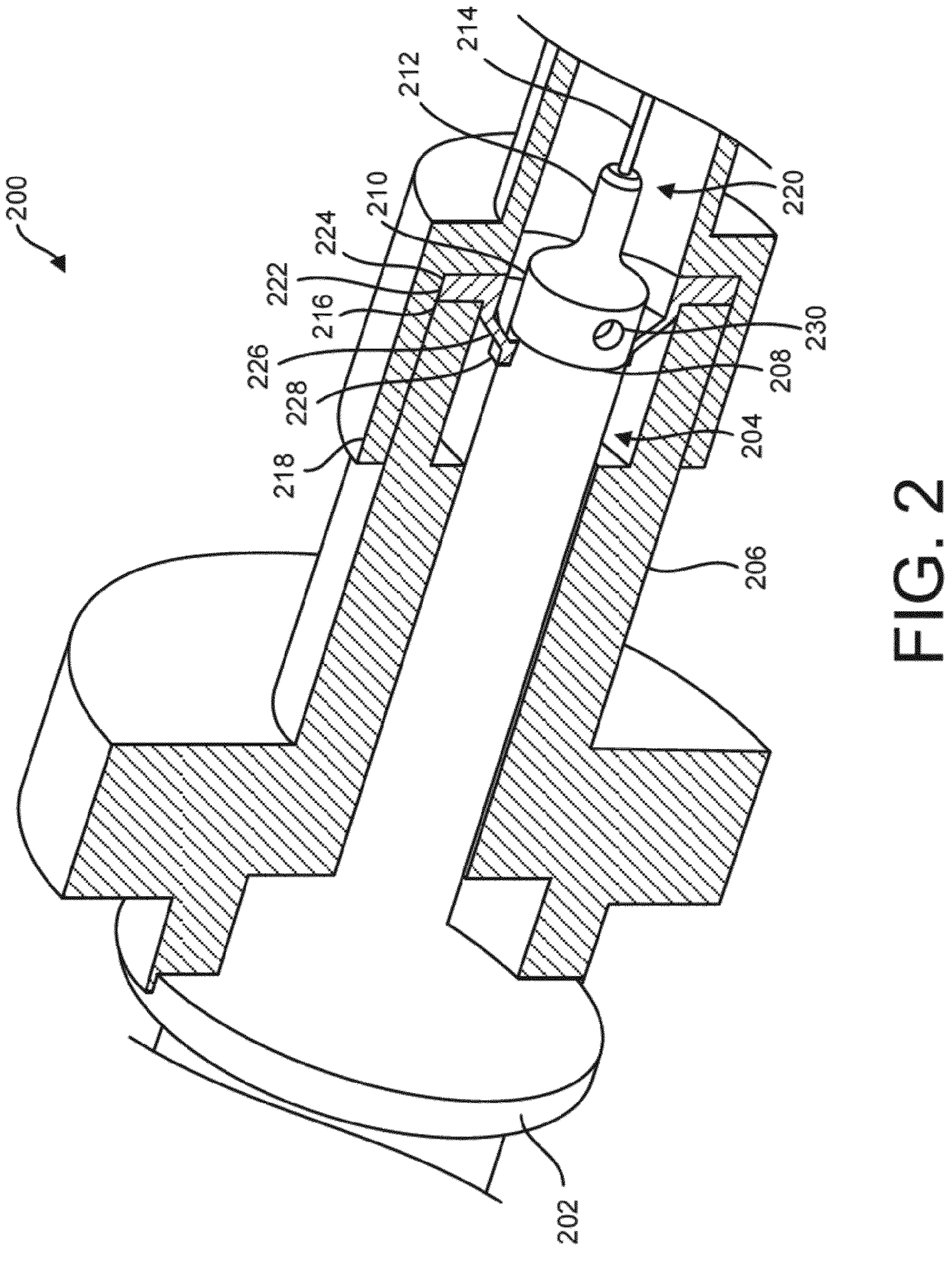
FIG. 2 is a perspective, partial sectional view of an ultrasonic therapy catheter system according to an embodiment of the present disclosure.
Figure 3:
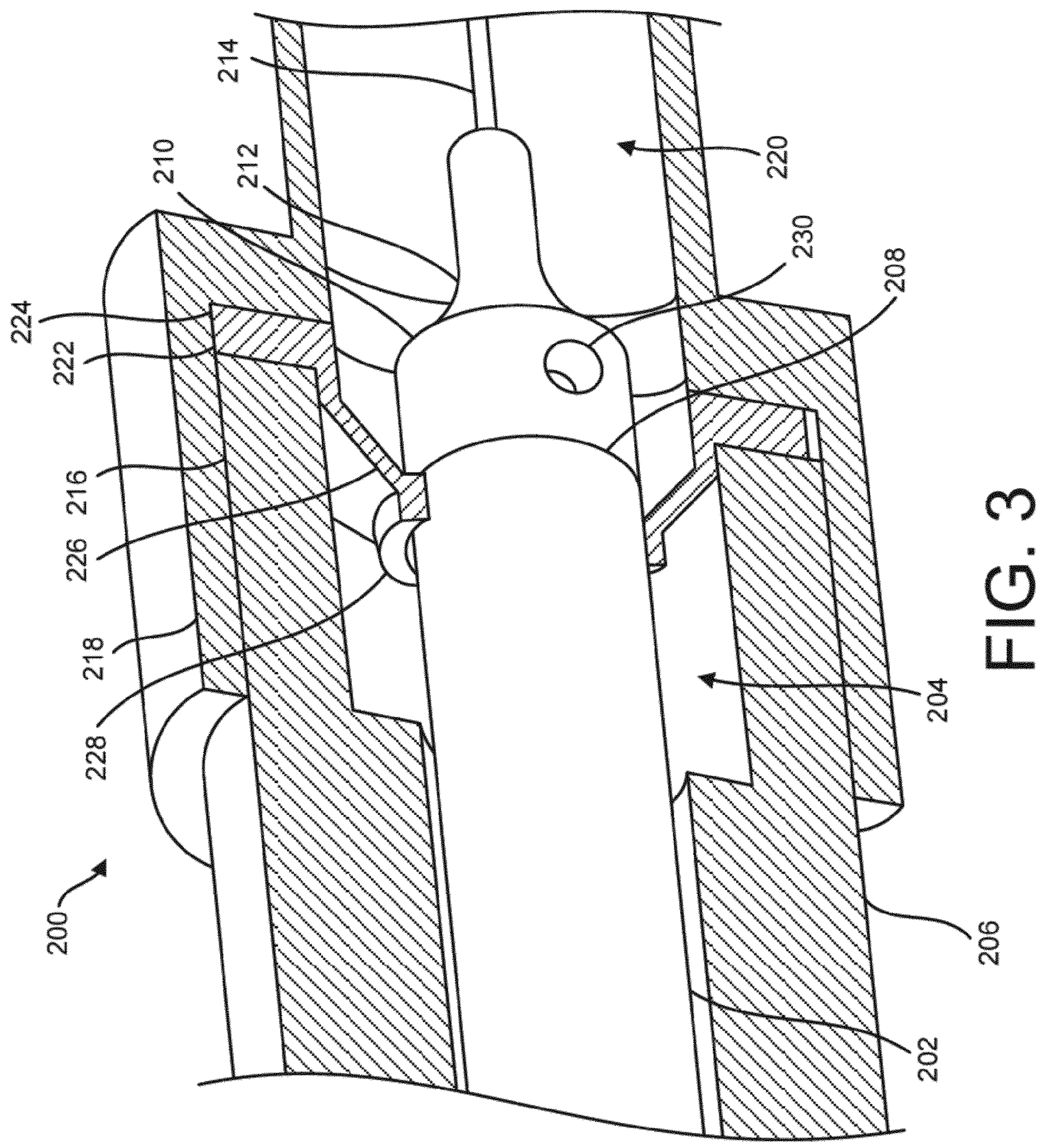
FIG. 3 is another perspective, partial sectional view of the ultrasonic therapy catheter system of FIG. 1.
Figure 4:
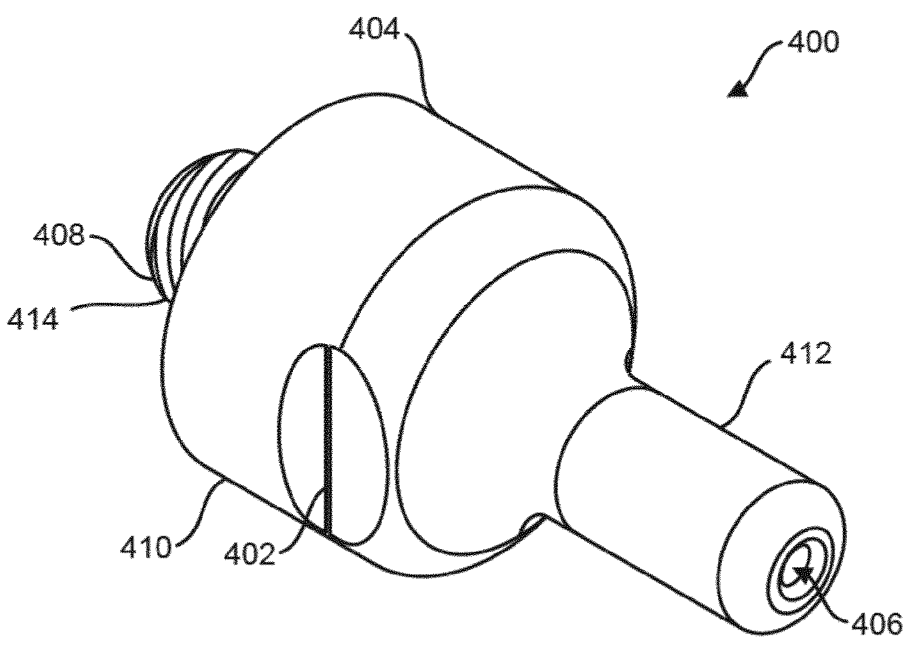
FIG. 4 is a perspective view of a sonic connector according to an embodiment of the present disclosure.
Figure 5:
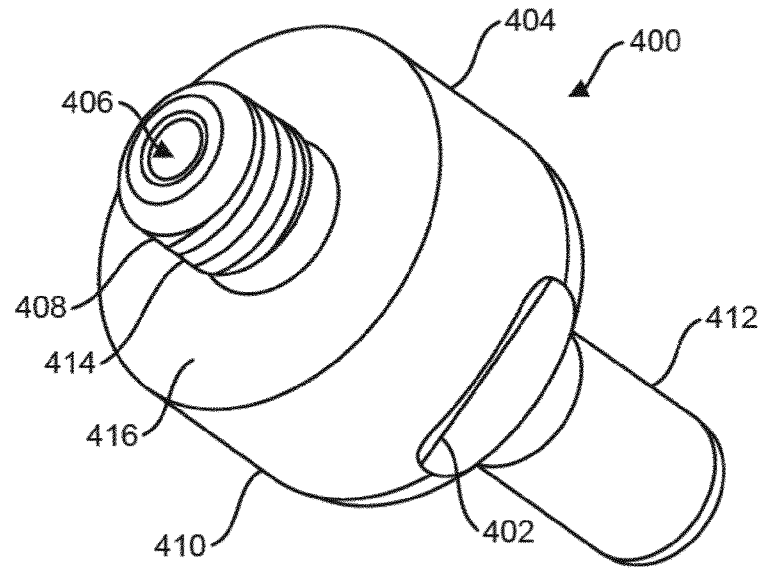
FIG. 5 is another perspective view of the sonic connector of FIG. 4.

Referring to FIGS. 2-3, an ultrasonic therapy catheter system 200 according to an exemplary embodiment of the present disclosure is illustrated in partial section. The system 200 includes an ultrasound generator 202, also referred to as an ultrasonic "horn," that is received in a passageway 204 of a shroud 206. At a distal end portion 208, the ultrasonic horn 202 detachably couples to a wire connector assembly 210. The wire connector assembly 210 generally includes a sonic connector 400, which detachably couples to the ultrasonic horn 202 and receives ultrasonic energy therefrom, and an elongated wire 900, which enters the vasculature of a subject, typically inside the lumen of a sheath (not shown), and receives and transmits ultrasonic energy to pulverize obstructions within a subject.

With continued reference to FIGS. 2-3, a distal end portion 216 of the shroud 206 detachably couples to a coupler 218. The coupler 218 generally receives the wire connector assembly 210 in a coupler passageway 220. The coupler 218 couples to a sheath (not shown) that receives the wire 900. The coupler 218 also couples to an auxiliary port (not shown) in fluid communication with the coupler passageway 220. As such, the auxiliary port facilitates delivering a fluid, such as saline, to the coupler passageway 220. To inhibit proximal flow into the shroud passageway 204, the distal end portion 208 of the shroud 206 carries a seal 222. More specifically and as illustrated, the shroud 206 carries a diaphragm seal 222 that sealingly engages the shroud 206 at an outer end portion 224. The outer end portion 224 couples to a proximally and inwardly extending flexible portion 226, and the flexible portion 226 couples to an opposite inner end portion 228. The inner end portion 228 sealingly engages the ultrasonic horn 202. Additionally, the flexible portion 226 of the diaphragm seal 222 flexes as the ultrasonic horn 202 delivers ultrasonic energy to the wire connector assembly 210. The seal 222 may comprise various flexible and medically-appropriate materials, such as polymers, and more specifically silicone.

FIGS. 4-8 illustrate a sonic connector 400 according to an exemplary embodiment of the present disclosure. The sonic connector 400 is generally similar to the sonic connector 212 described above, with the exception of including flat surfaces 402 as described below instead of a radially outwardly facing blind hole 230 (see FIGS. 2-3). The sonic connector 400 may be used in the ultrasonic therapy catheter system 200 shown in FIGS. 2-3 in lieu of the sonic connector 212. The sonic connector 400 may comprise any of various medically-appropriate materials, such as metals, and more specifically titanium grade 5. The sonic connector 400 generally includes a monolithic body 404 that defines an internal passageway 406, and the internal passageway 406 carries the wire 900 (shown elsewhere).

The body 404 generally includes a proximal end portion 408, an intermediate portion 410 coupled to the proximal end portion 408, and an opposite distal end portion 412 coupled to the intermediate portion 410. The proximal end portion 408 is configured to couple to the ultrasound generator 202 (shown elsewhere) via a threaded surface 414. The intermediate portion 410 is radially larger than the proximal end portion 408. The intermediate portion 410 includes a proximal ultrasound generator engagement surface 416 that is configured to engage the ultrasound generator 202. The intermediate portion 410 also includes flat surfaces 402 that facilitate coupling the sonic connector 400 to the ultrasonic generator 202. More specifically, the flat surfaces 402 facilitate grasping the sonic connector 400 with a tool, such as a spanner wrench. The intermediate portion 410 is illustrated as including two flat surfaces 402. In other embodiments, the intermediate portion 410 may have a different number of flat surfaces 402, such as three to eight flat surfaces 402. The distal end portion 412 is radially smaller than the intermediate portion 410.

Figures 6, 7:
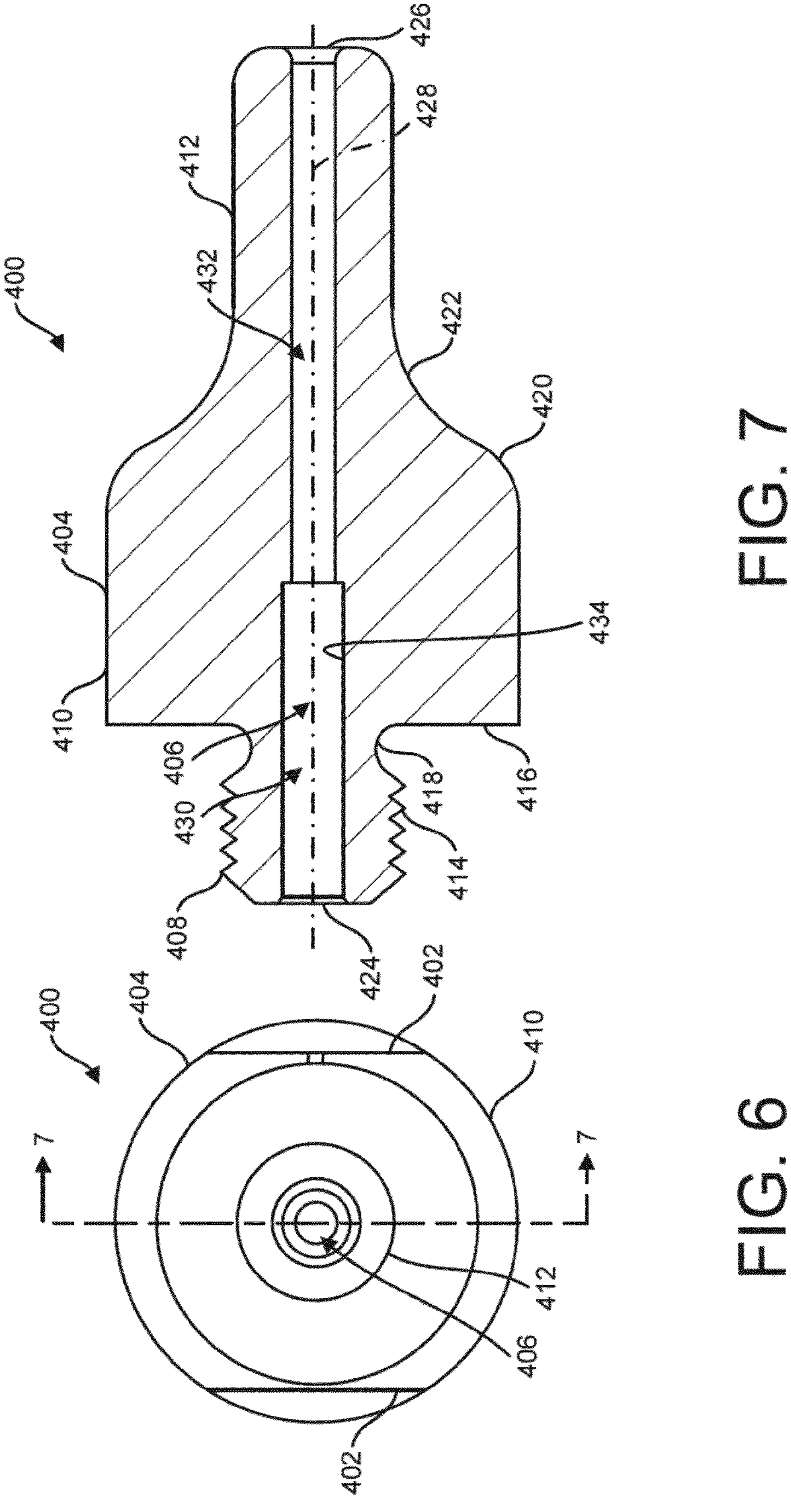
FIG. 6 is a proximal end view of the sonic connector of FIG. 4.
FIG. 7 is a sectional view of the sonic connector along line 7-7 of FIG. 6.
Figure 8:
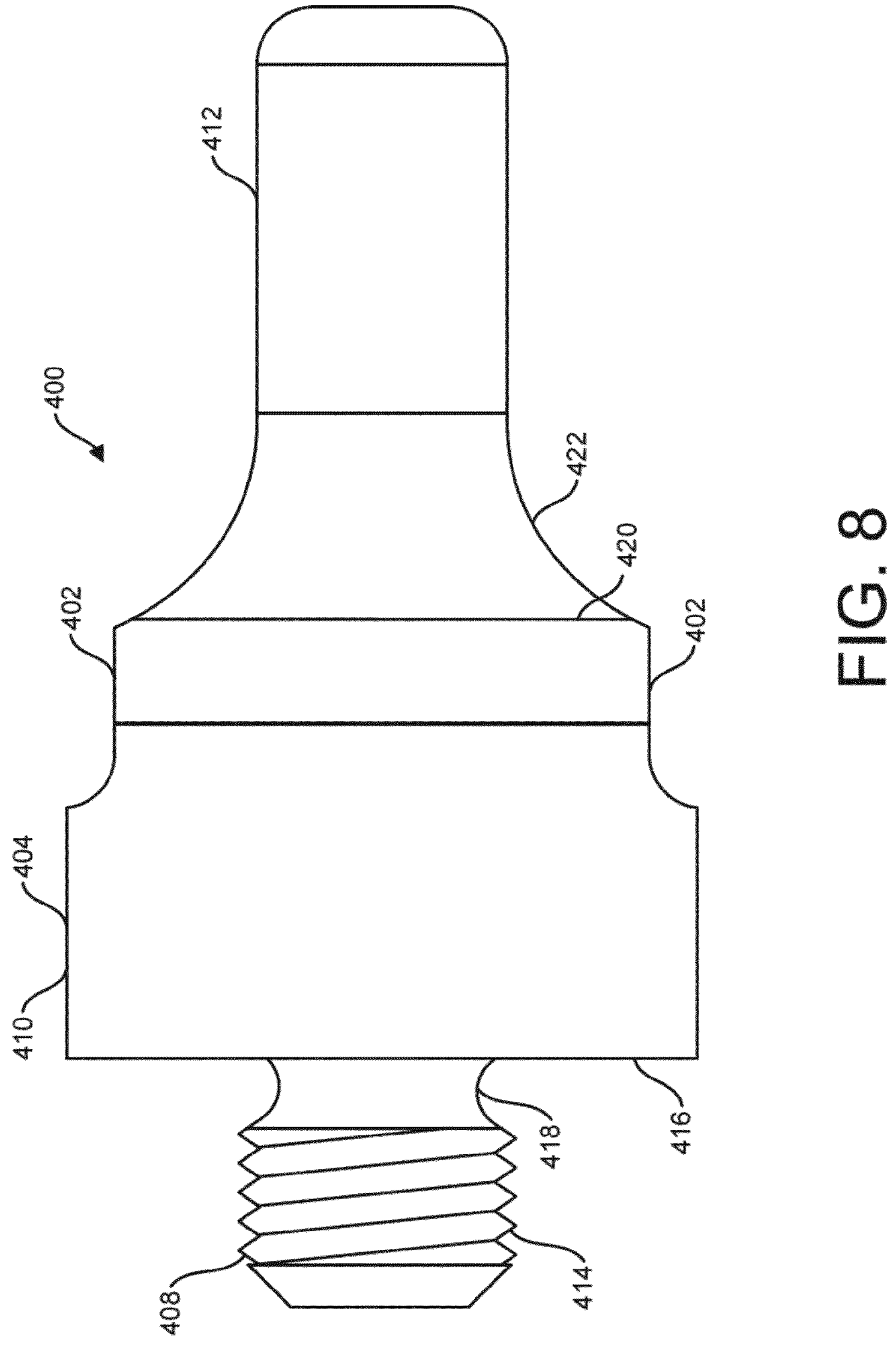
FIG. 8 is a side view of the sonic connector of FIG. 4.

With specific reference to FIGS. 7-8, the portions 408, 410, and 412 of the body 404 are coupled by multiple radii 418, 420, and 422. In some embodiments, the radii 418, 420, and 422 advantageously facilitate "funneling" ultrasonic waves relatively gradually and/or reduce or eliminate stress concentrations between the body portions 408, 410, and 412 compared to previous connectors. In some embodiments, the radii 418, 420, and 422 advantageously facilitate smooth ultrasonic wave transmission between the body portions 408, 410, and 412 compared to previous connectors.

With specific reference to FIG. 7 and as described briefly above, the body 404 of the sonic connector 400 defines an internal passageway 406. The passageway 406 extends from a proximal opening 424 at the proximal end portion 408 of the body 404 to a distal opening 426 at the distal end portion 412 of the body 404. The passageway 406 is also aligned with a longitudinal axis 428 of the body 404. The passageway 406 includes a proximal passageway portion 430 and a distal passageway portion 432. The proximal passageway portion 430 includes a tapered surface 434 that narrows proceeding proximally to distally. As described in further detail below, the tapered surface 434 engages and secures the sonic connector 400 to the wire 900 (shown elsewhere). In some embodiments, the tapered surface 434 tapers by substantially 6 percent (that is, 6 percent±1 percent). In some embodiments, the tapered surface 434 has dimensions consistent with a Morse taper. As described in further detail below, the distal passageway portion 432 is sized to slip fittingly receive the wire 900.

The sonic connector 400 may include any of the following exemplary dimensions. The sonic connector 400 may have a length along the longitudinal axis 428 of substantially 0.7 inches (that is, 0.7 inches±10 percent). Such a length is relatively short compared to previous connectors. In some embodiments, this short length advantageously reduces machining costs compared to those of previous connectors. Similarly, in some embodiments this short length facilitates forming the passageway 406 in the sonic connector 400. This in turn facilitates coupling the wire 900 to the sonic connector 400 near the proximal end portion 408, as described in further detail below. The intermediate portion 410 may have a diameter of substantially 0.344 inches (that is, 0.344 inches±10 percent). The distal end portion 412 may have a diameter of substantially 0.134 inches (that is, 0.134 inches±10 percent). The proximal end portion 408 may have a thread size appropriate for coupling to the ultrasonic horn 202 (shown elsewhere). The radius 418 may be substantially 0.04 inches (that is, 0.04 inches±10 percent). The radius 420 may be substantially 0.063 inches (that is, 0.063 inches±10 percent). The radius 422 may be substantially 0.125 inches (that is, 0.125 inches±10 percent).

Figures 9, 10:
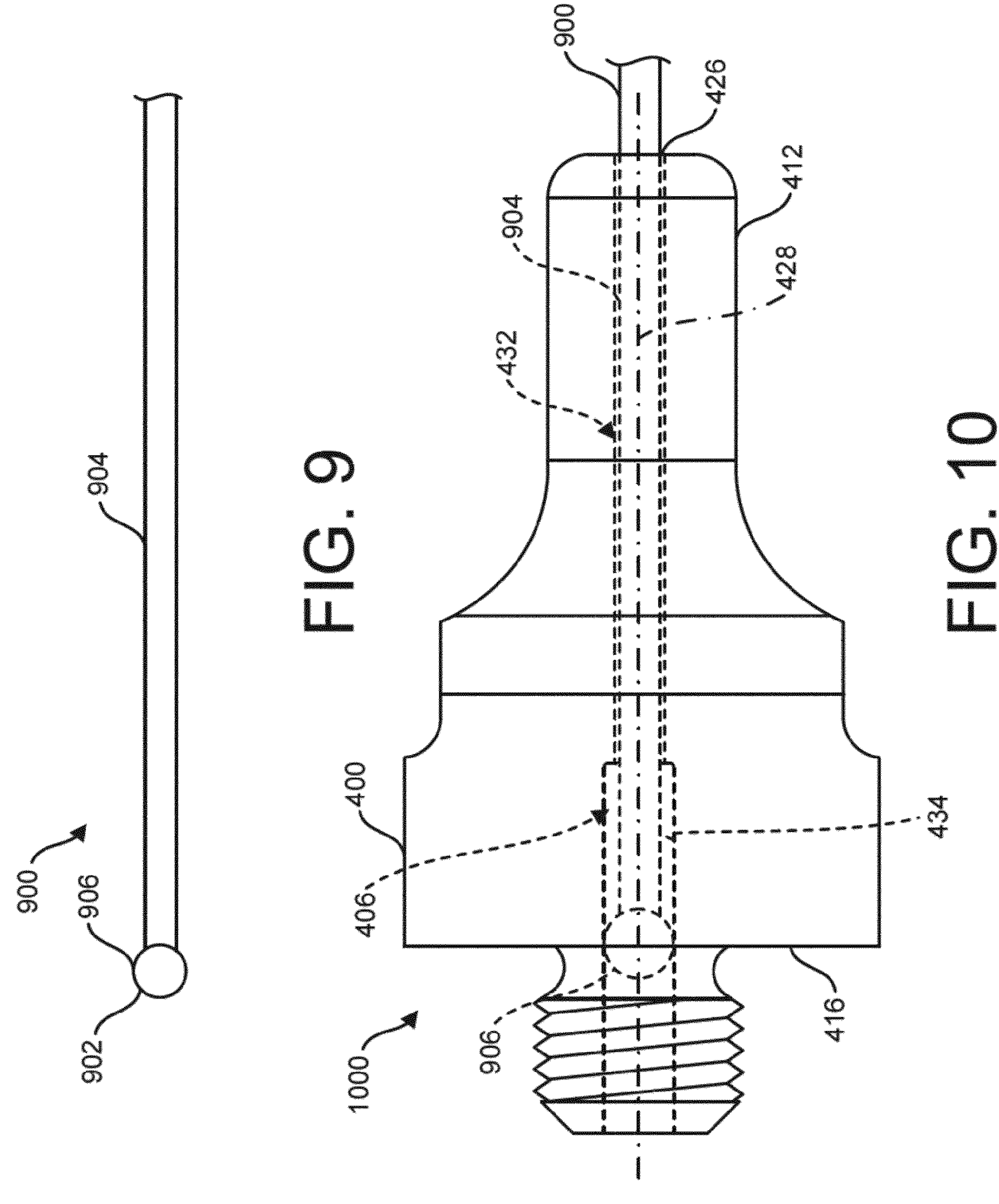
FIG. 9 is a side view of a wire according to an embodiment of the present disclosure.
FIG. 10 is a side view of a wire connector assembly including the sonic connector of FIG. 4 and the wire of FIG. 9.

FIG. 9 illustrates a wire 900 according to an exemplary embodiment of the present disclosure. The wire 900 may be the same wire 214 as described above in connection with FIGS. 2-3. The wire 900 generally includes a proximal end portion 902 and a narrower, distally extending, elongated portion 904. The proximal end portion 902 includes an engagement feature 906 that is configured to engage the tapered surface 434 of the sonic connector 400 (shown elsewhere) and thereby secure the wire 900 to the sonic connector 400. The engagement feature 906 is illustrated as being a ball. In other embodiments, the engagement feature 906 may have a different shape, such as a frusto-conical shape. The elongated portion 904 may have a generally uniform cross-sectional shape and size.

FIG. 10 illustrates a wire connector assembly 1000 including the sonic connector 400 and the wire 900. The wire connector assembly 1000 is generally similar to the wire connector assembly 210 described above, with the exception of the sonic connector 400 as described above. The wire connector assembly 1000 may be used in the ultrasonic therapy catheter system 200 shown in FIGS. 2-3 in lieu of the wire connector assembly 210. As illustrated, the engagement feature 906 of the wire 900 engages the tapered surface 434 of the passageway 406 of the sonic connector 400. More specifically, the engagement feature 906 engages the tapered surface 434 such that the engagement feature 906 is longitudinally aligned with the ultrasound generator engagement surface 416 of the sonic connector 400. In some embodiments, this advantageously facilitates relatively efficient transmission of ultrasonic energy from the ultrasonic horn 202 (shown elsewhere) to the wire 900 compared to previous systems. As described briefly above, the distal passageway portion 432 slip fittingly receives the elongated portion 904 of the wire 900. In some embodiments, this facilitates maintaining alignment of the wire 900 with the longitudinal axis 428, or stated another way, reducing or eliminating transverse motion of the wire 900 at the distal end portion 412 of the sonic connector 400. The elongated portion 904 extends outwardly and distally from the distal opening 426 of the passageway 406.

Figure 11:
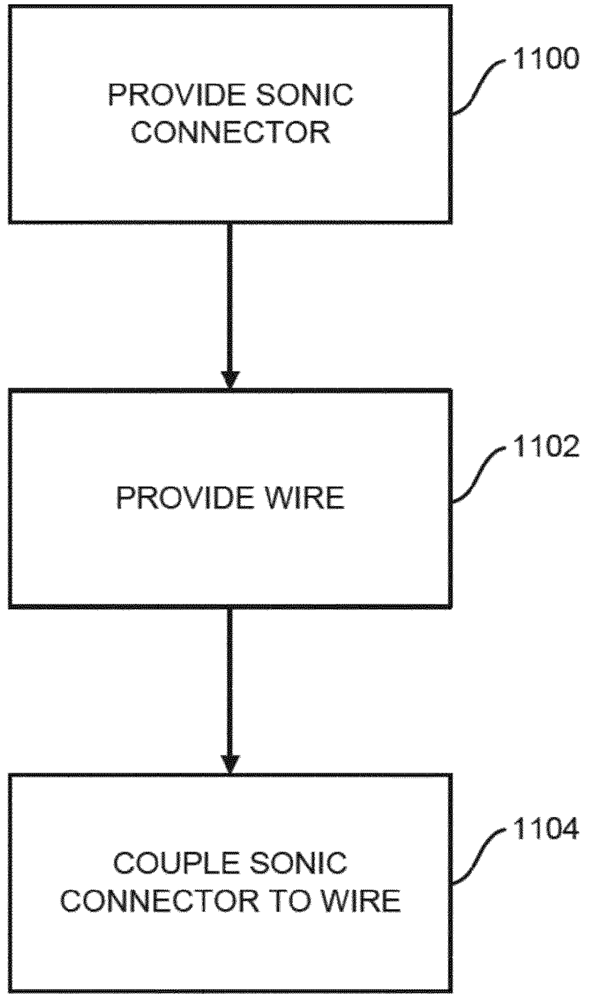
FIG. 11 is a flowchart illustrating a method of manufacturing a wire connector assembly according to an embodiment of the present disclosure.
Figure 12:
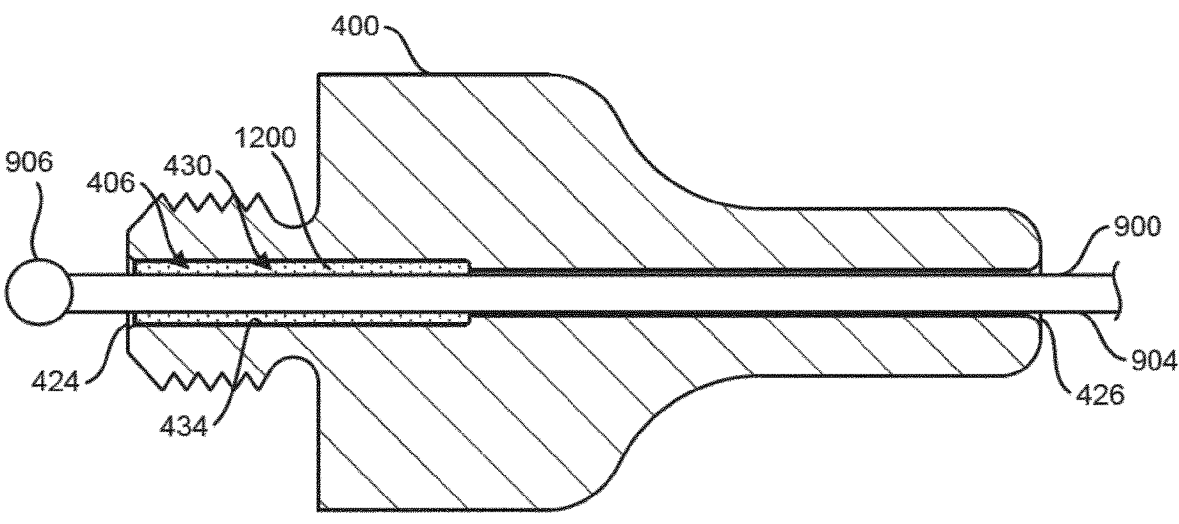
FIG. 12 is a sectional view of the sonic connector of FIG. 4 receiving the wire of FIG. 9.
Figure 13:
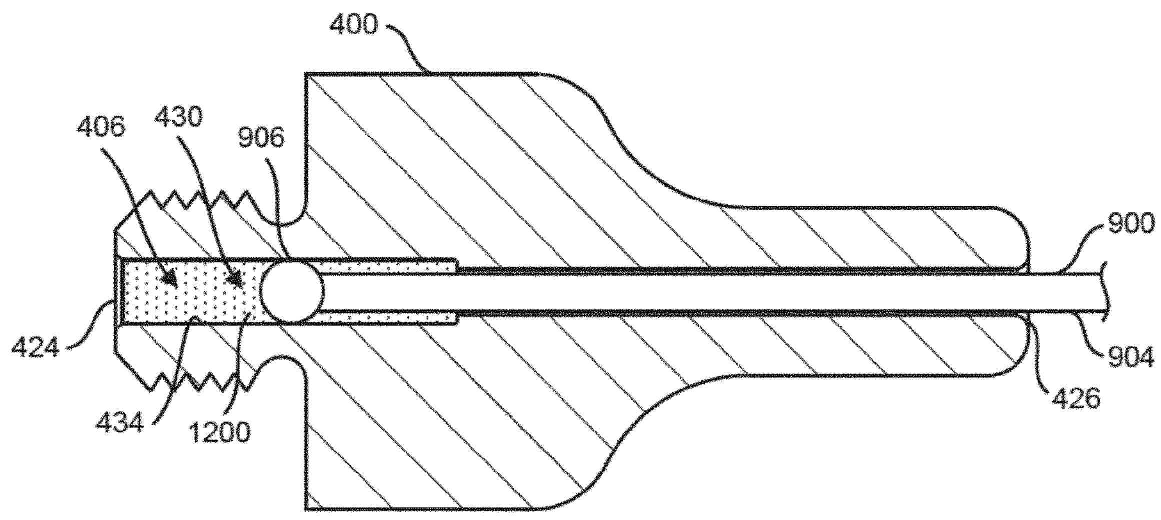
FIG. 13 is a sectional view of the sonic connector of FIG. 4 receiving the wire of FIG. 9 and engaging the wire with an internal tapered surface of the sonic connector.

Referring to FIGS. 11-13, a method of manufacturing the wire connector assembly 1000 according to an exemplary embodiment of the present disclosure is illustrated. FIG. 11 illustrates a flowchart including processes of the method of manufacturing the wire connector assembly 1000, and FIGS. 12-13 illustrate the wire connector assembly 1000 in partial cross section during several specific processes of the method. As shown in FIG. 11, the method includes providing the sonic connector 400 at block 1100. In some embodiments, this may include machining a short section of rod stock (such as titanium grade 5) to form the portions and other features of the sonic connector 400, such as the passageway 406 and the tapered surface 434. At block 1102, the wire 900 is provided. In some embodiments, this may include providing the elongated portion 904 and the engagement feature 906 and coupling them to each other. This may include, for example, coupling the engagement feature 906 to the elongated portion 904 via welding, crimping, and/or bonding. Alternatively, coupling the engagement feature 906 to the elongated portion 904 may include melting an end of the elongated portion 904 to form the engagement feature 906, and thereby monolithically coupling the engagement feature 906 to the elongated portion 904. At block 1104, the sonic connector 400 is coupled to the wire 900 such that the engagement feature 906 engages the tapered surface 434 and the elongated portion 904 extends outwardly from the distal opening 426 of the passageway 406. This may include, for example and as shown in FIGS. 12-13, moving the sonic connector 400 relative to the wire 900 such that the wire 900 passes through the proximal opening 424 of the passageway 406, the elongated portion 904 extends outwardly from a distal opening 426 of the passageway 406, and the engagement feature 906 engages the tapered surface 434. In some embodiments and as shown in FIGS. 12-13, the proximal passageway portion 430 may carry joining material 1200 (for example, an epoxy or adhesive) to facilitate securing the engagement feature 906 to the tapered surface 434. In some embodiments, the engagement feature 906 may be impacted (for example, by a pin) to facilitate securing the engagement feature 906 to the tapered surface 434. In some embodiments, the wire 900 and the sonic connector 400 may be subjected to an ultrasonic welding process to facilitate securing the engagement feature 906 to the tapered surface 434. In some embodiments, the sonic connector 400 may be subjected to a heating process prior to coupling to the wire 900 to facilitate securing the engagement feature 906 to the tapered surface 434 upon cooling.

The foregoing discussion has been presented for purposes of illustration and description. The foregoing is not intended to limit the disclosure to the form or forms disclosed herein. In the foregoing Summary for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A wire connector assembly for an ultrasonic therapy catheter system comprising an ultrasound generator, the wire connector assembly comprising:

a sonic connector configured to couple to the ultrasound generator and receive ultrasonic energy therefrom, the sonic connector comprising a body having a passageway extending therethrough, the passageway including a tapered surface; and a wire engaging the tapered surface and extending outwardly from the passageway, the wire configured to receive ultrasonic energy from the sonic connector.

2. The wire connector assembly of claim 1, wherein the wire comprises a proximal end portion including an engagement feature, the engagement feature engaging the tapered surface of the passageway of the sonic connector.

3. The wire connector assembly of claim 2, wherein the sonic connector further comprises:

a longitudinal axis aligned with the passageway; and an ultrasound generator engagement surface configured to engage the ultrasound generator, the ultrasound generator engagement surface being aligned with the engagement feature relative to the longitudinal axis.

4. The wire connector assembly of claim 2, wherein the engagement feature comprises a ball.

5. The wire connector assembly of claim 2, wherein the wire further comprises an elongated portion coupled to the engagement feature, wherein the passageway comprises a proximal passageway portion including the tapered surface and a distal passageway portion coupled to the proximal passageway portion, the distal passageway portion slip fittingly receiving the elongated portion of the wire.

6. The wire connector assembly of claim 1, wherein the sonic connector comprises a longitudinal axis aligned with the passageway, the sonic connector having a length along the longitudinal axis of substantially 0.7 inches.

7. A method of manufacturing a wire connector assembly for an ultrasonic therapy catheter system, the method comprising:

providing a sonic connector, the sonic connector comprising a body having a passageway extending therethrough, the passageway including a tapered surface;

providing a wire; and coupling the wire to the sonic connector such that the wire engages the tapered surface and extends outwardly from the passageway.

8. The method of claim 7, wherein providing the wire comprises:

providing an elongated portion;

providing an engagement feature; and coupling the engagement feature to the elongated portion;

and coupling the wire to the sonic connector comprises engaging the engagement feature with the tapered surface.

9. The method of claim 8, wherein coupling the engagement feature to the elongated portion comprises at least one of welding, crimping, and bonding the engagement feature to the elongated portion.

10. The method of claim 8, wherein coupling the engagement feature to the elongated portion comprises melting a proximal end portion of the wire.

11. The method of claim 8, wherein coupling the wire to the sonic connector comprises moving the sonic connector relative to the wire such that the wire passes through a proximal opening of the passageway, extends outwardly from a distal opening of the passageway, and the engagement feature engages the tapered surface.

12. The method of claim 8, wherein the sonic connector comprises a longitudinal axis aligned with the passageway and an ultrasound generator engagement surface configured to engage an ultrasound generator of the ultrasonic therapy catheter system, and wherein engaging the engagement feature with the tapered surface comprises aligning the engagement feature with the ultrasound generator engagement surface relative to the longitudinal axis.

13. The method of claim 8, wherein coupling the wire to the sonic connector further comprises positioning a joining material in a proximal portion of the passageway including the tapered surface.

14. The method of claim 8, wherein the engagement feature comprises a ball.

15. The method of claim 7, wherein the sonic connector comprises a longitudinal axis aligned with the passageway and a length along the longitudinal axis of substantially 0.7 inches.

* * * * *